(12) United States Patent
Wilk

(10) Patent No.: US 7,582,755 B2
(45) Date of Patent: Sep. 1, 2009

(54) CYANOPYRROLE-CONTAINING CYCLIC CARBAMATE AND THIOCARBAMATE BIARYLS AND METHODS FOR PREPARING THE SAME

(75) Inventor: Bogdan Kazimierz Wilk, New City, NY (US)

(73) Assignee: Wyeth, Madison, NJ (US)

( * ) Notice: Subject to any disclaimer, the term of this patent is extended or adjusted under 35 U.S.C. 154(b) by 702 days.

(21) Appl. No.: 11/113,795

(22) Filed: Apr. 25, 2005

(65) Prior Publication Data

US 2005/0239779 A1    Oct. 27, 2005

Related U.S. Application Data

(60) Provisional application No. 60/565,616, filed on Apr. 27, 2004.

(51) Int. Cl.
    C07D 265/12    (2006.01)
(52) U.S. Cl. ..................................... 544/92
(58) Field of Classification Search ............ 544/92
    See application file for complete search history.

(56) References Cited

U.S. PATENT DOCUMENTS

| 5,194,628 | A  | 3/1993 | Ackermann et al. |
| 6,387,992 | B1 | 5/2002 | Pastor et al. |
| 6,391,907 | B1 | 5/2002 | Fensome et al. |
| 6,407,101 | B1 | 6/2002 | Collins et al. |
| 6,436,929 | B1 | 8/2002 | Zhang et al. |
| 6,509,334 | B1 | 1/2003 | Zhang et al. |
| 6,562,857 | B2 | 5/2003 | Collins et al. |
| 6,566,358 | B2 | 5/2003 | Zhang et al. |
| 2002/0065192 | A1 | 5/2002 | MacKenzie et al. |
| 2003/0149273 | A1 | 8/2003 | Militzer et al. |

FOREIGN PATENT DOCUMENTS

| DE | 10111262 | 9/2002 |
| EP | 1308157 | 5/2003 |
| WO | WO-95/07275 | 3/1995 |
| WO | WO-00/50470 | 8/2000 |
| WO | WO 00/66560 A | 11/2000 |
| WO | WO 00/66570 A | 11/2000 |
| WO | WO 00/66571 A | 11/2000 |
| WO | WO 00/66581 A | 11/2000 |
| WO | WO-01/83571 | 11/2001 |
| WO | WO-01/96406 | 12/2001 |
| WO | WO-02/36641 | 5/2002 |
| WO | WO-02/36642 | 5/2002 |
| WO | WO-02/42281 | 5/2002 |
| WO | WO-03/031401 | 4/2003 |
| WO | WO-03/105860 | 12/2003 |

OTHER PUBLICATIONS

Collins et al., Novel Pyrrole-containing Progesterone Receptor Modulators, Bioorganic And Medicinal Chemistry Letters, 14 (2004), pp. 2185-2189.*

Bayly et al., "Structure-based design of COX-2 selectivity into flurbiprofen", *Bioorg. Med. Chem. Lett.* Feb. 8, 1999 9(3):307-312.

Caron et al., "Directed Ortho Metalation of Neopentyl Benzoates with LDA: Preparation of Arylboronic Acids", *J. Org. Chem.* Apr. 3, 1998 63(7):2054-2055.

Murase et al., "A synthesis of arcyriacyanin A, an unsymmetrically substituted indole pigment of the slime mould by palladium catalyzed cross-coupling reaction", *Chem. Pharm. Bull.* Jun. 1998 46(6):889-892.

Kristensen et al., "Synthesis of ortho substituted arylboronic esters by in situ trapping of unstable lithio intermediates", *Org. Lett.* May 17, 2001 10:I435-1437.

Molander et al., "Efficient Ligandless Palladium-Catalyzed Suzuki Reactions of Potassium Aryltrifluoroborates", *Org. Lett.* May 30, 2002 4:1867-1870.

Vazquez et al., "A non-cryogenic method for the preparation of 2-(indolyl) borates, silanes, and silanols", *J. Org. Chem.* Oct. 18, 2002 67(21):7551-7552.

Winkle et al., "Suzuki Reaction of a Diarylborinic Acid: One-Pot Preparation and Cross-Coupling of Bis(3,5-dimethylphenyl)borinic Acid", *Org. Proc. Res. Dev.* Jul. 2001 5(4):450-451.

Goosen, English Abstract of German Patent No. DE-10111262, issued Sep. 12, 2002.

* cited by examiner

*Primary Examiner*—James O Wilson
*Assistant Examiner*—Ebenezer Sackey
(74) *Attorney, Agent, or Firm*—Paul Carango, Esq.; Howson & Howson LLP

(57) ABSTRACT

Methods for preparing cyclic carbamates and thiocarbamates containing cyanopyrrole moieties and of the formula are provided.

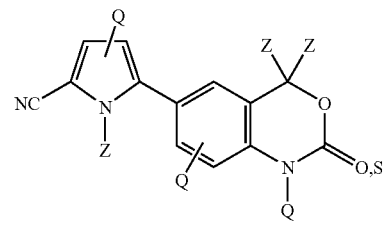

Z are the same or different and are H, optionally substituted $C_1$ to $C_6$ alkyl, or $COR^A$; $R^A$ is H, optionally substituted $C_1$ to $C_6$ alkyl, optionally substituted $C_1$ to $C_6$ alkoxy, or optionally substituted $C_1$ to $C_6$ aminoalkyl; Q are the same or different and are H, OH, $NH_2$, CN, halogen, optionally substituted $C_1$ to $C_6$ alkyl, optionally substituted $C_2$ to $C_6$ alkenyl, optionally substituted $C_1$ to $C_6$ alkynyl, optionally substituted $C_1$ to $C_6$ alkoxy, optionally substituted $C_1$ to $C_6$ aminoalkyl, or $COR^B$; and $R^B$ is H, optionally substituted $C_1$ to $C_6$ alkyl, optionally substituted $C_1$ to $C_6$ alkoxy, or optionally substituted $C_1$ to $C_6$ aminoalkyl.

Compounds including 2-amino-5-(5-cyano-1-methyl-1H-pyrrol-2-yl) benzoic acid methyl ester, 5-[4-amino-3-(1-hydroxy-1-methyl-ethyl)-phenyl]-1-methyl-1H-pyrrole-2-carbonitrile, and 2-amino-5-(5-cyano-1-methyl-1H-pyrrol-2-yl)-phenyl-ethanone, or pharmaceutically acceptable salts thereof, and the uses thereof are also provided.

17 Claims, No Drawings

CYANOPYRROLE-CONTAINING CYCLIC CARBAMATE AND THIOCARBAMATE BIARYLS AND METHODS FOR PREPARING THE SAME

CROSS-REFERENCE TO RELATED APPLICATIONS

This application claims the benefit of the priority of U.S. Provisional Patent Application No. 60/565,616, filed Apr. 27, 2004.

BACKGROUND OF THE INVENTION

The present invention is drawn to methods for preparing cyclic carbamate and thiocarbamate compounds.

Methods for preparing cyanopyrrole-containing cyclic carbamate and thiocarbamate biaryls have been described in U.S. Pat. Nos. 6,509,334; 6,566,358; 6,436,929; 6,407,101; and 6,562,857. Such compounds are useful as progesterone receptor (PR) modulators, which are pharmaceutically useful for a variety of indications including contraception; the treatment and/or prevention of dysfunctional bleeding, uterine myometrial fibroids, uterine leiomyomata, endometriosis, benign prostatic hypertrophy, polycystic ovary syndrome, carcinomas, and adenocarcinomas; the synchronization of the estrus in livestock; and the stimulation of food intake.

Current methods for preparing cyclocarbamate compounds substituted at the 6-position with bromine substituents entail at least three steps and utilize expensive reagents, including 1,1-carbonyldiimidazole and 1,1-thiocarbonyldiimidazole.

Conversion of the cyclocarbamate to the cyclothiocarbamate further requires a fourth step utilizing a thionating agent. Such methods typically form a variety of impurities, including pyrrole thioamide impurities. These methods also entail many steps, are expensive, and are troublesome.

What is needed in the art are more efficient methods for preparing cyclocarbamate and cyclothiocarbamate compounds.

SUMMARY OF THE INVENTION

In one aspect, a method for producing 6-(cyanopyrrole)-cyclocarbamate or cyclothiocarbamate compounds is provided and includes the steps of (a) reacting a cyanopyrrole with a coupling agent; (b) reacting the product of (a) with an anthranilate or nitroester thereof; (c) reacting the product of (b) with an organometallic nucleophile; and (d) converting the product of (d) to the 6-(cyanopyrrole)-cyclocarbamate or cyclothiocarbamate compound.

In another aspect, a method for producing 6-(cyanopyrrole)-cyclocarbamate or 6-(cyanopyrrole)-cyclocarbamate compounds is provided and includes the steps of (a) reacting a cyanopyrrole with a coupling agent; (b) reacting the product of (a) with an anthranilic alcohol or nitro alcohol thereof; and (c) converting the product of (b) to the 6-(cyanopyrrole)-cyclocarbamate or 6-(cyanopyrrole)-cyclothiocarbamate compound.

In a further aspect, a method for producing 6-(cyanopyrrole)-cyclocarbamate or 6-(cyanopyrrole)-cyclocarbamate compounds is provided and includes the steps of (a) reacting a cyanopyrrole with a coupling agent; (b) reacting the product of (a) with an anthranilic ketone or nitro ketone thereof; and (c) converting the product of (b) to the 6-(cyanopyrrole)-cyclocarbamate or 6-(cyanopyrrole)-cyclothiocarbamate compound.

In yet another aspect, a method for producing 6-(cyanopyrrole)-cyclothiocarbamate compounds is provided and includes the steps of (a) reacting a cyanopyrrole with a coupling agent; (b) reacting the product of (a) with a bromoanthranilate or bromoanthranilate nitroester; (c) reacting the product of (b) with an organometallic nucleophile; and (d) converting the product of (c) to the 6-(cyanopyrrole)-cyclothiocarbamate.

In still a further aspect, a method for producing 6-(cyanopyrrole)-cyclothiocarbamate compounds is provided and includes the steps of (a) reacting a cyanopyrrole with a coupling agent; (b) reacting the product of (a) with a bromoanthranilic alcohol or bromoanthranilic alcohol nitro alcohol; and (c) converting the product of (b) to 6-(cyanopyrrole)-cyclothiocarbamate.

In another aspect, a method for producing 6-(cyanopyrrole)-cyclothiocarbamate compounds is provided and includes the steps of (a) reacting a cyanopyrrole with a coupling agent; (b) reacting the product of (a) with a bromoanthranilic ketone or bromoanthranilic nitro ketone; and (c) converting the product of (b) to 6-(cyanopyrrole)-cyclothiocarbamate.

In still a further aspect, a method for producing cyanopyrrole anthranilates or nitroesters thereof is provided and includes the steps of (a) reacting a cyanopyrrole with a coupling agent; and (b) reacting the product of (a) with an anthranilate.

In another aspect, a method for producing a cyanopyrrole anthranilic alcohol or nitro alcohol thereof is provided and includes the steps of (a) reacting a cyanopyrrole with a coupling agent; (b) reacting the product of (a) with an anthranilic alcohol or nitro alcohol thereof; and (c) reacting the product of (b) with an organometallic nucleophile.

In yet a further aspect, a method for producing a cyanopyrrole anthranilic ketone or nitro ketone thereof is provided and includes the steps of (a) reacting a cyanopyrrole with a coupling agent; (b) reacting the product of (a) with an anthranilic ketone or nitro ketone thereof; and (c) reacting the product of (b) with an organometallic nucleophile.

In yet a further aspect, compounds of the following formulas are provided:

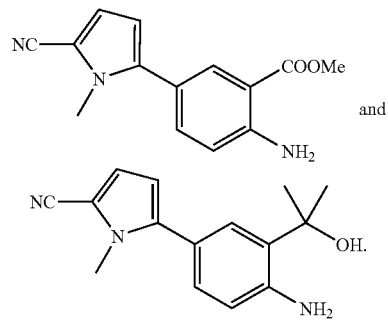

Other aspects and advantages of the present invention are described further in the following detailed description of the preferred embodiments thereof.

DETAILED DESCRIPTION OF THE INVENTION

The present invention provides methods for producing cyclocarbamate and cyclothiocarbamate compounds and cyanopyrrole-containing compounds, and derivatives thereof. Specifically, the present invention provides more efficient methods for preparing cyclocarbamate and cyclothiocarbamate compounds and cyanopyrrole-containing compounds.

The method of the present invention typically includes (a) reacting an optionally substituted cyanopyrrole with a coupling agent; (b) reacting the product of (a) with an anthranilate, anthranilate nitroester, anthranilic ketone, or anthranilic nitro ketone; (c) converting the product of (b) to the corresponding alcohol; and (d) forming the cyclocarbamate or cyclothiocarbamate. Step (c) can be omitted if step (b) includes reacting the product of (a) with an anthranilic alcohol or nitro alcohol thereof. See, Scheme 1, where Q, Z, M, M', and L are defined below.

I. Definitions

The term "coupling agent" as used herein refers to a compound that directly or indirectly promotes the coupling of two or more chemical compounds (depicted as M-M' in the above-noted Scheme 1). A variety of coupling agents is known to those of skill in the art and includes magnesium, zinc, silicon, tin, or boron compounds. Desirably, the coupling agent is a trialkylborate such as tri-isopropylborate, zinc halide such as zinc chloride or zinc bromide, or a magnesium halide such as magnesium chloride or magnesium bromide. See, International Patent Publication No. WO 03/105860.

The term "coupling group" as used herein refers to a substituent that results from a coupling agent and becomes

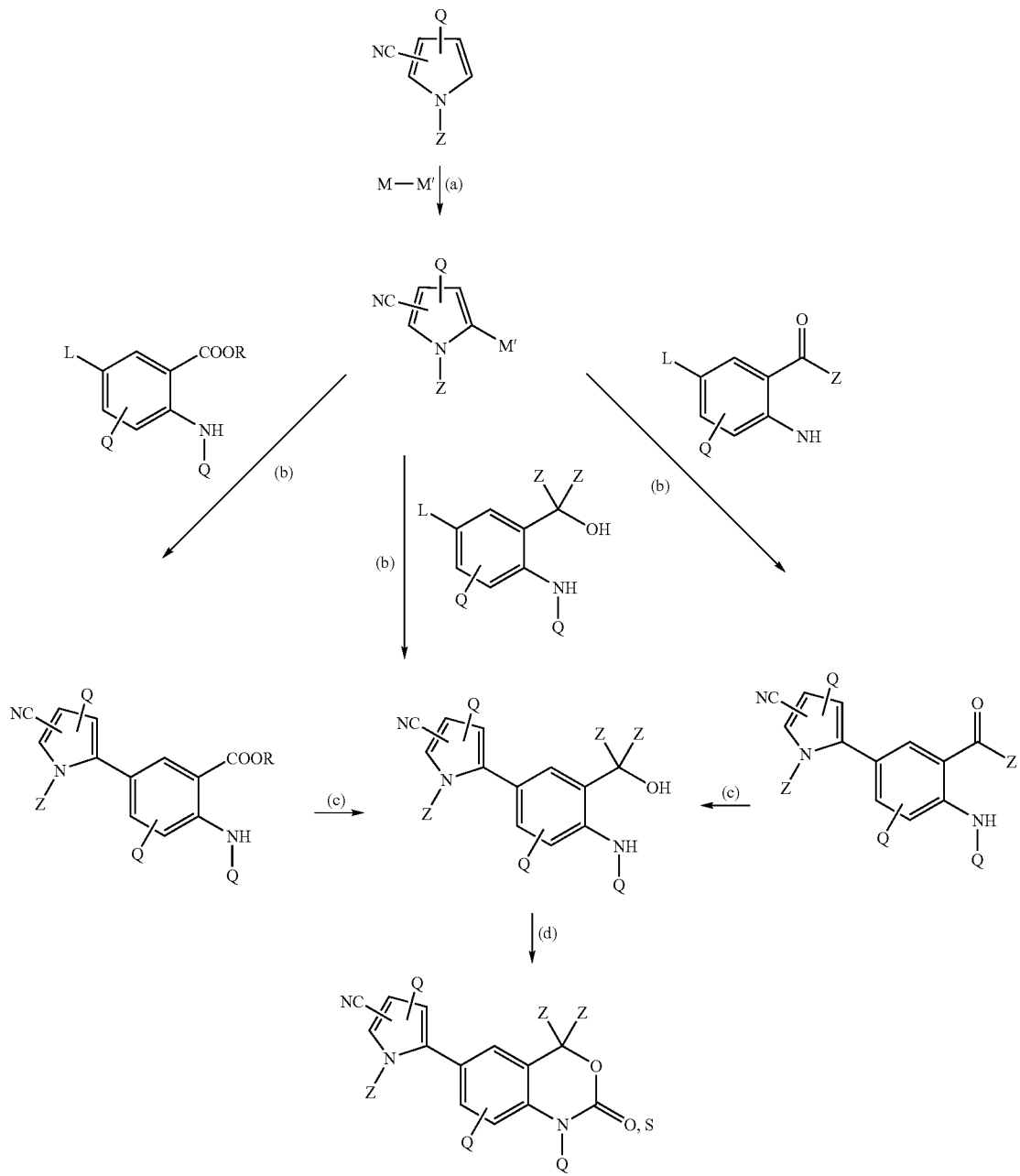

attached thereto the cyanopyrrole compound (depicted as M' in the above-noted Scheme 1). This group can be displaced upon reaction with other reagents, such as the anthranilate and nitroesters thereof and anthranilic alcohols and nitro alcohols thereof as set forth above in Scheme 1 and below the description thereof. The particular coupling group utilized in the present invention is dependent upon the specific reaction being performed and can readily be determined by one of skill in the art. Common coupling groups include, without limitation, magnesium, zinc, silicon, tin, or boron substituents. In one embodiment, the coupling groups are boron moieties including boronate salts, borinate salts, boronic acids, borinic acids, boronic esters, borinic esters such as the ester noted below, and trihaloborate salts such as trifluoroborate salts ($BF_3^-$), zinc halides, magnesium moieties, diazonium salts ($N_2^+$), tosylates (OTs), mesylates (OMs), and copper moieties. In a further embodiment, the coupling groups are boron moieties including boronic acids, borinic acids, boronic esters, borinic acids such as the borate ester noted below, trihaloborate salts such as trifluoroborate salts ($BF_3^-$), zinc halides, or magnesium moieties.

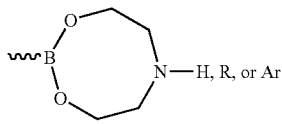

where: R is alkyl group; and
Ar is an aryl group
borinic ester

The term "catalyst" as used herein refers to a compound that promotes the coupling of 2 compounds. Typically, the catalyst contains a transition metal and one or more ligands attached thereto. A variety of transition metals can be used in the present invention and includes Pd and Ni metals, among others. Several ligands can be bound to the transition metal and include, without limitation, acetate, hydroxyl, nitrile, halide, and phosphine substituents. Many transition metal complexes containing such ligands that can be used as the catalysts are commercially available and include those recited on the Strem website. In one embodiment, the catalyst is tetrakis(triphenylphosphine)palladium.

The term "ligand" as used herein refers to a substituent that is bound to a transition metal.

The term "alkyl" is used herein to refer to both straight- and branched-chain saturated aliphatic hydrocarbon groups having 1 to about 10 carbon atoms, and desirably about 1 to about 8 carbon atoms. The term "alkenyl" is used herein to refer to both straight- and branched-chain alkyl groups having one or more carbon-carbon double bonds and containing about 2 to about 10 carbon atoms. In one embodiment, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bonds and having 2 to about 8 carbon atoms. In one embodiment, the term alkynyl refers to an alkyl group having 1 or 2 carbon-carbon triple bonds and having 2 to about 6 carbon atoms.

The terms "substituted alkyl" refers to an group having one or more substituents including, without limitation, halogen, CN, OH, $NO_2$, amino, aryl, heterocyclic, alkoxy, aryloxy, alkylcarbonyl, alkylcarboxy, and arylthio, which groups can be optionally substituted. These substituents can be attached to any carbon of an alkyl, alkenyl, or alkynyl group provided that the attachment constitutes a stable chemical moiety.

The term "aryl" as used herein refers to an aromatic system e.g., of 6 to 14 carbon atoms, which can include a single ring or multiple aromatic rings fused or linked together where at least one part of the fused or linked rings forms the conjugated aromatic system. In one embodiment, the aryl groups include phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. In one embodiment, a substituted aryl group is substituted with 1 to about 4 substituents.

The term "heterocyclic" as used herein refers to a stable 4- to 7-membered monocyclic or 9-15 membered multicyclic heterocyclic ring which is saturated, partially unsaturated, or wholly unsaturated. The heterocyclic ring has carbon atoms and one or more heteroatoms including nitrogen, oxygen, and sulfur atoms. In one embodiment, the heterocyclic ring has 1 to about 4 heteroatoms in the backbone of the ring. In another embodiment, when the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring, e.g., of 9-15 ring members. In yet another embodiment, the heterocyclic ring can be attached to the aryl ring through a heteroatom or carbon atom provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings. The term "substituted heterocyclic" as used herein refers to a heterocyclic group having one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. Preferably, a substituted heterocyclic group is substituted with 1 to about 4 substituents.

The term "aminoalkyl" as used herein refers to both secondary and tertiary amines where the point of attachment is through the nitrogen-atom and the alkyl groups are optionally substituted. The alkyl groups can be the same or different.

The term "halogen" as used herein refers to Cl, Br, F, or I groups.

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "arylthio" as used herein refers to the S(aryl) group, where the point of attachment is through the sulfur-atom and the aryl group can be optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "leaving group" as used herein refers to a substituent that is present on a chemical compound and can be displaced (the term L as used herein refers to a leaving group). The particular leaving group utilized in the present invention is dependent upon the specific reaction being performed and can readily be determined by one of skill in the art. Common leaving groups include, without limitation, halides and sulfonates ($OSO_2R^1$). In one embodiment, the leaving group is a halide such as bromine, chlorine, or iodine, and more preferably is bromine. The term "strong non-nucleophilic base" as used herein refers to a compound that abstracts a hydrogen atom from a molecular complex. In one embodiment, the strong non-nucleophilic base does not interact with any other substituents on the molecular complex or the reagents utilized in the reaction. In another embodiment, the strong non-nucleophilic base is lithium di-isopropyl amide (LDA). A number of strong non-nucleophilic bases are known to those of skill in the art and include di-isopropyl amine salts. See, e.g., the strong non-nucleophilic bases commercially available at http://www.fmclithium.com (the FMC Lithium website).

The term "organometallic nucleophile" as used herein refers to a compound that reacts with a compound having an acidic hydrogen atom. A number of organometallic nucleophiles are known in the art and include Grignard agents and lithium agents such as alkyl lithium agents. In one embodiment, the organometallic nucleophile is a Grignard agent such as R'MgX, wherein R' is an alkyl such as a methyl group or R' is an aryl group, such as a phenol, and X is a halogen such as bromine or chlorine. In a further embodiment, the Grignard agent is methylmagnesium bromide which is typically utilized as a solution (e.g., 1.4 M solution) in a mixture of toluene and THF at reduced temperatures. In one embodiment, the Grignard agent is a 80:20 to 70:30 mixture of toluene:THF, or about a 75:25 mixture of toluene:THF. Reduced temperatures typically range from −7° to −0° C., but lower or higher temperatures can be utilized depending on the reaction being performed and conditions of the reaction. In another embodiment, the organometallic nucleophile is an alkyl lithium agent such as methyl lithium, ethyl lithium, propyl lithium or butyl lithium.

The term "purified" or "pure" as used herein refers to a compound that contains less than about 10% impurities. In one embodiment, the term "purified" or "pure" refers to a compound that contains less than about 5% impurities, less than about 2% impurities, or less than about 1% impurities. The term "purified" or "pure" can also refer to a compound that contains about 0% impurities.

By the term "dry" or "drying" is meant a procedure by which entrapped solvents, including organic solvents, or water, or volatile solids are removed.

The term "boronate" or "boronate salt" as used herein refers to a compound having a —B(O-substituent)$_3$ group attached thereto, wherein the substituent forms a stable bond to an O-atom attached to the boron atom and a countercation (denoted by the term $CC^+$ as used herein) is present to form the stable compound. In one embodiment, the counteraction is a Group I or II alkali or alkaline earth metal including lithium, sodium, potassium, cesium, magnesium calcium, strontium, or barium, among others.

The term "borinate" or "borinate salt" as used herein refers to a compound having a —B(O-substituent)$_2$- group attached thereto, wherein the substituent forms a stable bond to an O-atom attached to the boron atom and a countercation (denoted by the term $CC^+$ as used herein and defined above) is present to form the stable compound.

The term "boronic ester" as used herein refers to a compound having a —B(O-substituent)$_2$ group attached thereto, wherein the substituent forms a stable bond to an O-atom attached to the boron atom.

The term "borinic ester" as used herein refers to a compound having a —B(O-substituent)- group attached thereto, wherein the substituent forms a stable bond to an O-atom attached to the boron atom.

The term "boronic acid" as used herein refers to a compound having a —B(OH)$_2$ group attached thereto.

The term "borinic acid" as used herein refers to a compound having a —B(OH)— group attached thereto.

II. Methods of the Invention

The method of the present invention is drawn to preparing cyclocarbamate and cyclothiocarbamate compounds, preferably containing cyanopyrrole substituents, and derivatives thereof. In one embodiment, 2-cyanopyrrole containing cyclocarbamate and cyclothiocarbamate compounds are prepared according to the present invention. In another embodiment, compounds having the following structures are prepared according to the present invention:

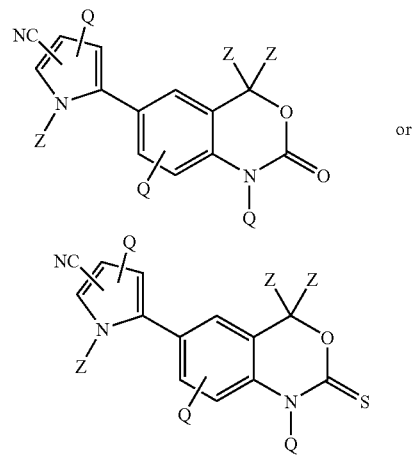

wherein:

Z are the same or different and are H, $C_1$ to $C_6$ alkyl, substituted $C_1$ to $C_6$ alkyl, or $COR^A$. $R^A$ is selected from among H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl.

Q are the same or different and are selected from among H, OH, NH$_2$, CN, halogen, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_1$ to C$_6$ alkoxy, substituted C$_1$ to C$_6$ alkoxy, C$_1$ to C$_6$ aminoalkyl, substituted C$_1$ to C$_6$ aminoalkyl, or COR$^B$. R$^B$ is selected from among H, C$_1$ to C$_6$ alkyl, substituted C$_1$ to C$_6$ alkyl, C$_1$ to C$_6$ alkoxy, substituted C$_1$ to C$_6$ alkoxy, C$_1$ to C$_6$ aminoalkyl, or substituted C$_1$ to C$_6$ aminoalkyl.

In a further embodiment, compounds of the following formula are prepared according to the present invention.

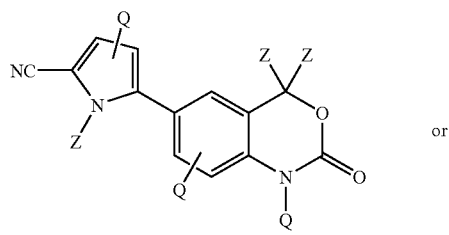

or

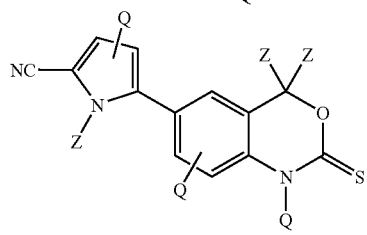

5-(4,4-dimethyl-2-oxo-1,4-dihydro-2H-benzooxazin-6-yl)-1-methyl-1H-pyrrole-2-carbonitrile and 5-(4,4-dimethyl-2-thioxo-1,4-dihydro-2H-benzooxazin-6-yl)-1-methyl-1H-pyrrole-2-carbonitrile can therefore be prepared according to the present invention.

In one embodiment, a cyanopyrrole of the following structure is reacted with a coupling agent as defined above. The CN group of the following structure can be bound to any carbon-atom of the five-membered ring, including the 2-, 3-, 4-, or 5-position of the ring.

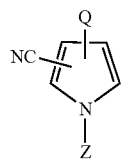

In a further embodiment, the cyanopyrrole utilized with the coupling agent is a 2-cyanopyrrole, or a 2-cyanopyrrole having the following structure, where Q and Z are defined above. In yet another embodiment, the cyanopyrrole is 1-methylpyrrole-2-carbonitrile.

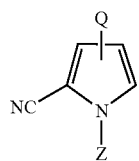

Upon reaction of the cyanopyrrole with the coupling agent, a compound of the following structure is formed, where Q and Z are defined above.

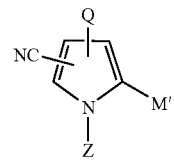

In one embodiment, the following 2-cyanopyrrole borate salts, or derivatives thereof, are prepared upon reaction of the cyanopyrrole with the coupling agent. In these compounds, CC$^+$ denotes a counter-cation (countercation) from the strong non-nucleophilic base that interacts with the base molecule to form a stable compound and Q, Z, and CC$^+$ are as defined above.

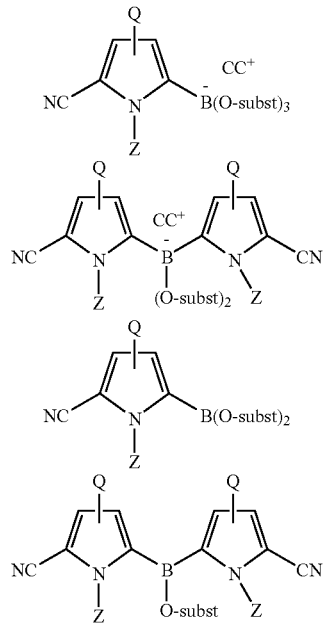

In another embodiment, the following 2-cyanopyrrole borate salts, or derivatives thereof, are prepared upon reaction of the cyanopyrrole with the coupling agent.

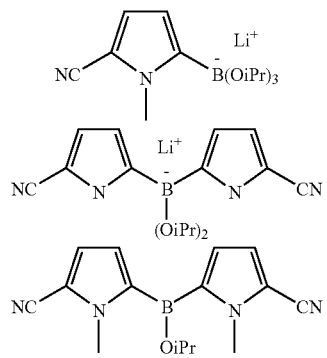

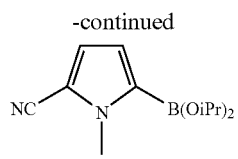

In a further embodiment, the following boronic acids, borinic acids, cyanopyrrole boronic acids, and cyanopyrrole borinic acids are prepared. Such boronic and borinic acids are typically isolated in situ and utilized in further reactions. The boronic and borinic acids are prepared using the borate salt as described above and hydrolyzing the borate salt. See, Scheme 2, where substituents Q, Z, and CC$^+$ are defined above. In another embodiment, hydrolyzing is accomplished using water which may contain other agents including mineral acids such as hydrochloric acid. In still a further embodiment, the boronic acid is (5-Cyano-1-methyl-1H-pyrrol-2-yl)-boronic acid.

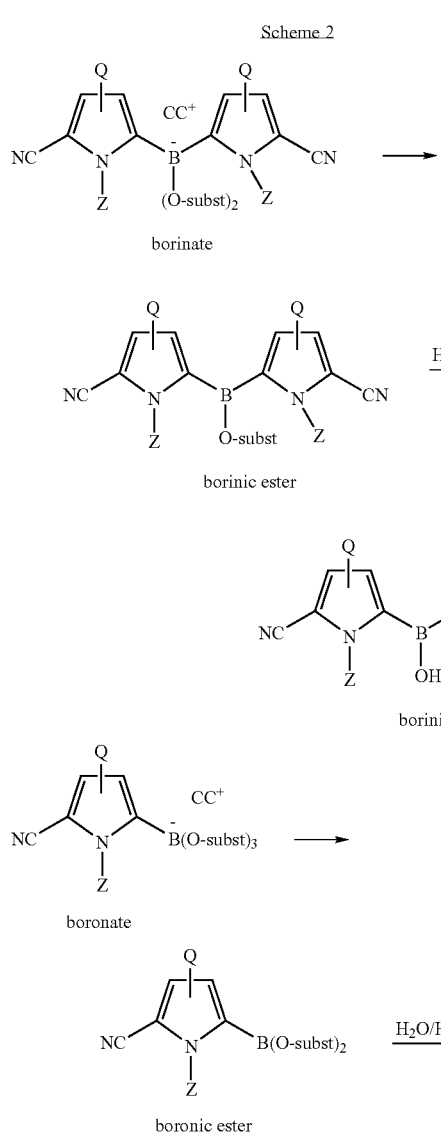

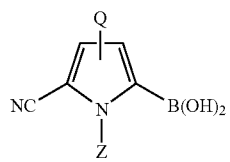

In yet a further embodiment, the following cyanopyrrole boronic and borinic acids are prepared according to the present invention, where Q and Z are defined above.

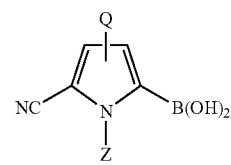

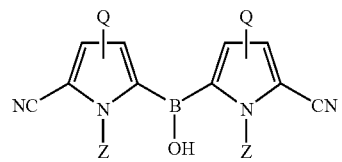

In still another embodiment, the following cyanopyrrole boronic and borinic acids are prepared according to the present invention.

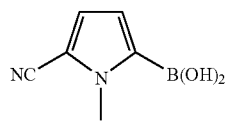

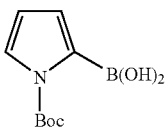

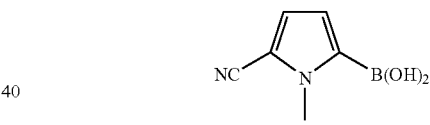

In yet another embodiment, the trifluoroborate salts and cyanopyrrole trifluoroborate salts are prepared by combining a fluoride agent with a borate salt as described above. A number of fluoride agents can be utilized to prepare the trifluoroborate salts and include reagents such as hydrogen fluoride, or derivatives thereof including potassium hydrogen fluoride, among others. One of skill in the art would readily be able to determine a suitable fluoride agent to utilize in the present invention.

In still a further embodiment, the following trifluroborate salt can be prepared according to the present invention.

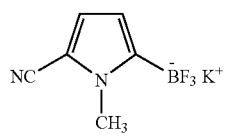

Additional compounds can be added to promote reaction between the cyanopyrrole and coupling agent and include strong non-nucleophilic bases including LDA. One of skill in the art would readily be able to select other additional agents for use in the coupling reaction.

Subsequent to the reaction between the cyanopyrrole and coupling agent, the product of the same is reacted with an optionally substituted anthranilate, anthranilate nitro ester, anthranilic alcohol, anthranilic nitro alcohols, anthranilic ketone, or anthranilic nitro ketone.

(i) Coupling the Cyanopyrrole with an Anthranilate or Nitro Ester thereof

The product of the reaction between the cyanopyrrole and coupling agent can be reacted with an optionally substituted anthranilate or nitroester thereof to form a cyanopyrrole substituted anthranilate. Desirably, the anthranilate or nitroester thereof is optionally substituted with a leaving group (L) and can have the following structures.

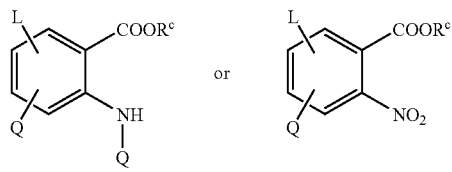

wherein:

Q are the same or different and are H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ alkoxy, substituted $C_1$ to $C_6$ alkoxy, $C_1$ to $C_6$ aminoalkyl, substituted $C_1$ to $C_6$ aminoalkyl, or $COR^B$;

$R^B$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;

$R^C$ is $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ aminoalkyl, or substituted $C_1$ to $C_6$ aminoalkyl;

L is halogen or $OSO_2R^1$; and $R^1$ is $CF_3$, $C_1$ to $C_6$ alkyl, or substituted $C_1$ to $C_6$ alkyl.

Desirably, L is a halogen or alkyl sulfonate leaving group and the anthranilate is further substituted with amino or nitro groups.

In a further embodiment, the anthranilate or nitroester thereof has the following structure:

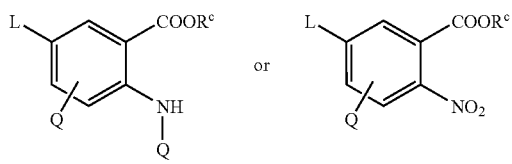

wherein, L, Q, and $R^C$ are defined above.

In another embodiment, the anthranilate is bromoanthranilate or methyl-2-amino-5-bromo benzoate.

The cyanopyrrole-substituted anthranilate or nitroester thereof prepared according to the present invention typically has the following structure:

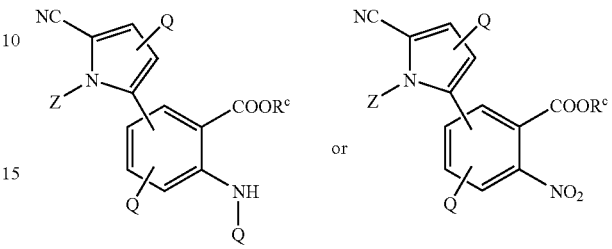

wherein:

Z is H, $C_1$ to $C_6$ alkyl, substituted $C_1$ to $C_6$ alkyl, or $COR^A$;

$R^A$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;

Q are the same or different and are H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ alkoxy, substituted $C_1$ to $C_6$ alkoxy, $C_1$ to $C_6$ aminoalkyl, substituted $C_1$ to $C_6$ aminoalkyl, or $COR^B$;

$R^B$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl; and $R^C$ is $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ aminoalkyl, or substituted $C_1$ to $C_6$ aminoalkyl.

Desirably, the cyanopyrrole-substituted anthranilate or nitroester thereof prepared according to the present invention is a compound of the following structure

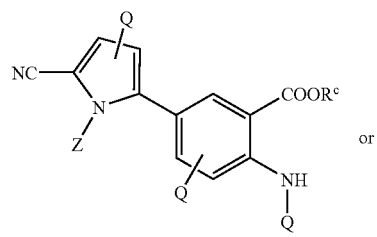

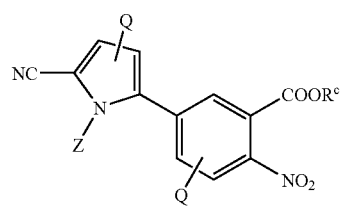

In a further embodiment, 2-amino-5-(5-cyano-1-methyl-1H-pyrrol-2-yl)benzoic acid methyl ester is prepared according to the present invention.

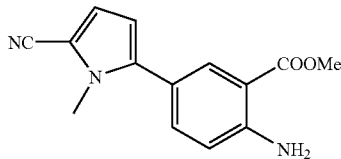

The cyanopyrrole substituted anthranilate and anthranilate nitroester can be converted to a cyanopyrrole substituted anthranilic alcohol or nitro alcohol thereof using an organometallic nucleophile such as a Grignard reagent or lithium reagent. Without wishing to be bound by theory, the inventors have discovered that the organometallic nucleophile utilized in the present invention preferentially adds to the ester group of the cyanopyrrole-substituted anthranilate or nitroester thereof and not the undesirable cyano group of the pyrrole.

(ii) Coupling the Cyanopyrrole with an Anthranilic Ketone or Nitro Ketone thereof Alternatively, the product of the reaction between the cyanopyrrole and coupling agent is reacted with an optionally substituted anthranilic ketone or nitro ketone thereof to form a cyanopyrrole substituted anthranilic ketone. In one embodiment, the anthranilic ketone or nitro ketone thereof utilized in the present invention is optionally substituted with a leaving group (L) and can have the following structures:

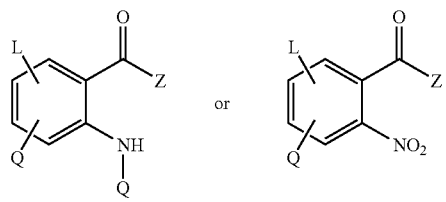

In a further embodiment, the anthranilic ketone or nitro ketone thereof has the following structure:

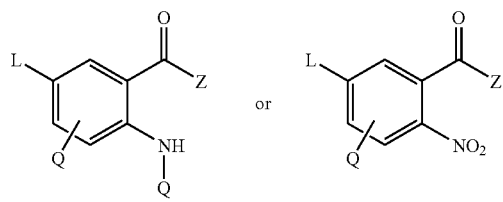

In another embodiment, the anthranilic ketone or nitro ketone thereof contains a halogen or alkyl sulfonate leaving group. In still another embodiment, the anthranilic ketone is bromoanthranilic ketone or 1-(2-amino-5-bromo-phenyl)-ethanone.

Typically, the cyanopyrrole-substituted anthranilic ketone or nitro ketone thereof prepared according to the present invention is a compound of the following structure:

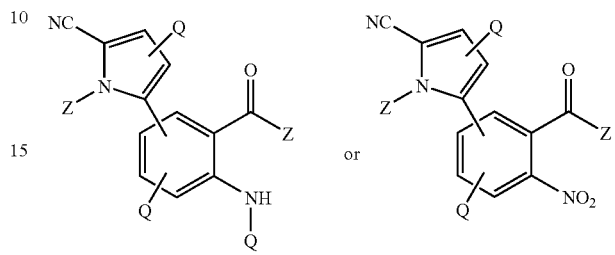

Desirably, the cyanopyrrole-substituted anthranilic ketone or nitro ketone thereof prepared according to the present invention is a compound of the following structure

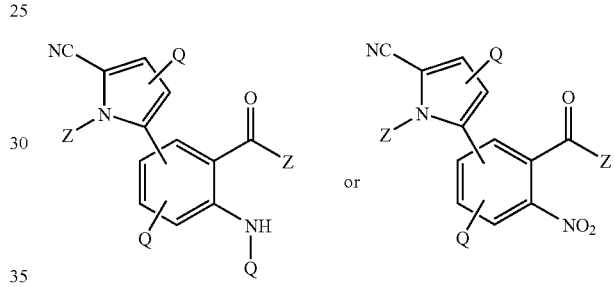

In a further embodiment, 2-amino-5-(5-cyano-1-methyl-1H-pyrrol-2-yl)-phenyl-ethanone is prepared according to the present invention.

The cyanopyrrole substituted anthranilic ketone and anthranilic nitro ketone thereof can then be converted to a cyanopyrrole substituted anthranilic alcohol or nitro alcohol thereof using an organometallic nucleophile such as a Grignard reagent or lithium reagent as described above.

(iii) Coupling the Cyanopyrrole with an Anthranilic Alcohol or Nitro Alcohol thereof An anthranilic alcohol or nitro alcohol thereof is alternatively utilized in place of the anthranilate, anthranilate nitroester, anthranilic ketone, or anthranilic nitro ketone to form the cyanopyrrole substituted anthranilic alcohol or nitro alcohol thereof. By doing so, conversion of the cyanopyrrole substituted anthranilate or nitroester thereof to the corresponding cyanopyrrole anthranilic alcohol or nitro alcohol thereof can be avoided.

This method includes reacting an anthranilic alcohol or nitro alcohol thereof with the product of the reaction between the cyanopyrrole and coupling agent. The anthranilic alcohol or nitro alcohol thereof is substituted with a leaving group (L) such as a halogen or alkyl sulfonate group and optionally substituted with other substituents such as amino or nitro groups. In one embodiment, this reaction is performed in the presence of a catalyst, such as tetrakis(triphenylphosphine) palladium, among others.

In a further embodiment, the anthranilic alcohol or nitro alcohol thereof has the following structure, where Z and Q are defined above.

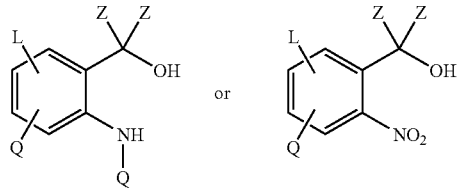

In another embodiment, the anthranilic alcohol or nitro alcohol thereof has the following structure, where Z and Q are defined above.

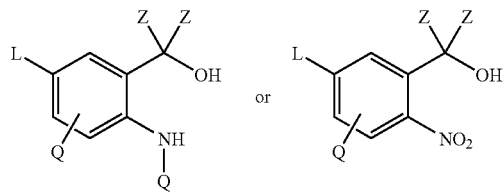

In still a further embodiment, the anthranilic alcohol is bromoanthranilic alcohol which is described in detail in International Patent Publication No. WO 00/66570.

Typically, the cyanopyrrole-substituted anthranilic alcohol or nitro alcohol thereof of the following structure is prepared according to the present invention:

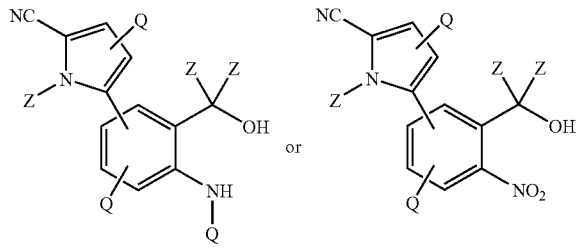

wherein:

Z are the same or different and are selected from among H, $C_1$ to $C_6$ alkyl, substituted $C_1$ to $C_6$ alkyl, or $COR^A$. $R^A$ is selected from among H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl. Q are the same or different and are selected from among H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ alkoxy, substituted $C_1$ to $C_6$ alkoxy, $C_1$ to $C_6$ aminoalkyl, substituted $C_1$ to $C_6$ aminoalkyl, or $COR^B$. $R^B$ is selected from among H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl.

Desirably, the cyanopyrrole-substituted anthranilic alcohol or nitro alcohol thereof of the following structure is prepared according to the present invention:

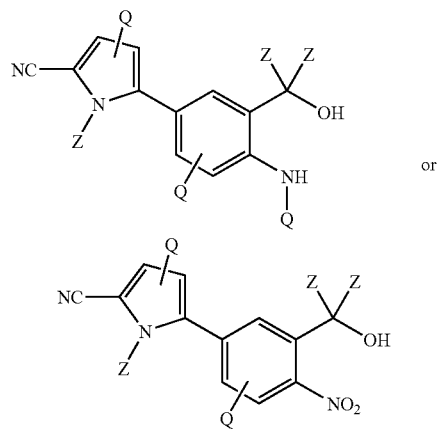

In a further embodiment, the following cyanopyrrole-substituted anthranilic alcohol is 5-[4-amino-3-(1-hydroxy-1-methyl-ethyl)-phenyl]-1-methyl-1H-pyrrole-2-carbonitrile.

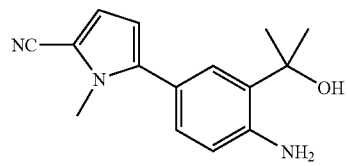

Prior to cyclizing the anthranilate nitro ester, anthranilic nitro alcohol, or anthranilic nitro ketone, the same must independently be converted to the corresponding anthranilate, anthranilic alcohol, or anthranilic ketone, respectively, by reduction. One of skill in the art would readily be able to select suitable reducing agent to carry out these reductions. A number of reducing agents useful for this purpose are known and include, without limitation, those set forth in R.C. Larock, "Comprehensive Organic Transformations", VCH Publishers, Inc., New York, N.Y., 1989, which is hereby incorporated by reference.

The cyanopyrrole substituted anthranilic alcohol can thereby be converted to the cyanopyrrole substituted cyclocarbamate or cyclothiocarbamate compound. Typically, this is performed using a cyclizing agent. A variety of cyclizing agents are known to those of skill in the art and include, without limitation, phosgene, thiophosgene, triphosgene, 1,1'-carbonyldiimidazole (CDI), 1,1'-thiocarbonyldiimidazole (TCDI), carbon disulfide at elevated temperatures such as 80° C., or carbon disulfide in the presence of a base such as ethanolic KOH, NaOH, imidazole, tertiary bases such as triethylamine or triphenylphosphine, polycarbonate, chloroformates such as trichloromethylchloroformate, or trichloromethanesulfenyl chloride.

In one embodiment, the present invention provides a method for producing 6-(cyanopyrrole)-cyclocarbamate or cyclothiocarbamate compounds including the steps of (a) reacting a cyanopyrrole with a coupling agent; (b) reacting the product of (a) to form a cyanopyrrole substituted anthranilic alcohol or nitro alcohol thereof; (c) reducing the anthranilic nitro alcohol to the anthranilic alcohol; and (d) converting the cyanopyrrole substituted alcohol to the 6-(cyanopyrrole)-cyclocarbamate or cyclothiocarbamate compound.

In another embodiment, the present invention provides a method for producing 6-(cyanopyrrole)-cyclocarbamate or 6-(cyanopyrrole)-cyclothiocarbamate compounds including the steps of (a) reacting a cyanopyrrole with a coupling agent; (b) reacting the product of (a) with an anthranilate or nitroester thereof; (c) reacting the product of (b) with an organometallic nucleophile; and (d) converting the product of (c) to the 6-(cyanopyrrole)-cyclocarbamate or 6(cyanopyrrole)-cyclothiocarbamate compound.

In another embodiment, the present invention provides a method for producing 6-(cyanopyrrole)-cyclocarbamate or 6-(cyanopyrrole)-cyclothiocarbamate compounds including the steps of (a) reacting a cyanopyrrole with a coupling agent; (b) reacting the product of (a) with an anthranilate or nitroester thereof; (c) reacting the product of (b) with an organometallic nucleophile; (d) optionally reducing the cyanopyrrole anthranilate nitro ester to the cyanopyrrole anthranilate; and (e) converting the cyanopyrrole anthranilate to the 6-(cyanopyrrole)-cyclocarbamate or 6(cyanopyrrole)-cyclothiocarbamate compound.

In a further embodiment, the present invention provides a method for producing 6-(cyanopyrrole)-cyclocarbamate or 6-(cyanopyrrole)-cyclothiocarbamate compounds including the steps of (a) reacting a cyanopyrrole with a coupling agent; (b) reacting the product of (a) with an anthranilic alcohol or nitro alcohol thereof; and (c) converting the product of (b) to the 6-(cyanopyrrole)-cyclocarbamate or 6(cyanopyrrole)-cyclothiocarbamate compound.

In yet another embodiment, the present invention provides a method for producing 6-(cyanopyrrole)-cyclocarbamate or 6-(cyanopyrrole)-cyclothiocarbamate compounds including the steps of (a) reacting a cyanopyrrole with a coupling agent; (b) reacting the product of (a) with an anthranilic alcohol or nitro alcohol thereof; (c) reducing the cyanopyrrol anthranilic nitro alcohol to the cyanopyrrole anthranilic alcohol; and (d) converting the cyanopyrrole anthranilic alcohol to the 6-(cyanopyrrole)-cyclocarbamate or 6-(cyanopyrrole)-cyclothiocarbamate compound.

In a further embodiment, the present invention provides a method for producing 6-(cyanopyrrole)-cyclocarbamate or 6-(cyanopyrrole)-cyclothiocarbamate compounds including the steps of (a) reacting a cyanopyrrole with a coupling agent; (b) reacting the product of (a) with an anthranilic ketone or nitro ketone thereof; and (c) converting the product of (b) to the 6-(cyanopyrrole)-cyclocarbamate or 6(cyanopyrrole)-cyclothiocarbamate compound.

In still another embodiment, the present invention provides a method for producing 6-(cyanopyrrole)-cyclocarbamate or 6-(cyanopyrrole)-cyclothiocarbamate compounds including the steps of (a) reacting a cyanopyrrole with a coupling agent; (b) reacting the product of (a) with an anthranilic ketone or nitro ketone thereof; (c) reducing the cyanopyrrole anthranilic nitro ketone to the cyanopyrrole anthranilic ketone; and (d) converting the anthranilic ketone to the 6-(cyanopyrrole)-cyclocarbamate or 6(cyanopyrrole)-cyclothiocarbamate compound.

In yet another embodiment, the present invention provides a method for producing 6-(cyanopyrrole)-cyclothiocarbamate compounds including the steps of: (a) reacting a cyanopyrrole with a coupling agent; (b) reacting the product of (a) with bromoanthranilate or nitroester thereof; (c) reacting the product of (b) with an organometallic nucleophile; and (d) converting the product of (c) to the 6-(cyanopyrrole)-cyclothiocarbamate compound.

In still another embodiment, the present invention provides a method for producing 6-(cyanopyrrole)-cyclothiocarbamate compounds including the steps of (a) reacting a cyanopyrrole with a coupling agent; (b) reacting the product of (a) with bromoanthranilic alcohol or nitro alcohol thereof; and (c) converting the product of (b) to the 6-(cyanopyrrole)-cyclothiocarbamate compound.

In another embodiment, the present invention provides a method for producing 6-(cyanopyrrole)-cyclothiocarbamate compounds including the steps of (a) reacting a cyanopyrrole with a coupling agent; (b) reacting the product of (a) with bromoanthranilic ketone or nitro ketone thereof; and (c) converting the product of (b) to the 6-(cyanopyrrole)-cyclothiocarbamate compound.

In yet another embodiment, the present invention provides a method for producing cyanopyrrole anthranilates including the steps of (a) reacting a cyanopyrrole with a coupling agent; and (b) reacting the product of (a) with an anthranilate or nitroester thereof.

In another embodiment, the present invention provides a method for producing a cyanopyrrole anthranilic alcohol or nitro alcohol thereof including the steps of (a) reacting a cyanopyrrole with a coupling agent; (b) reacting the product of (a) with an anthranilate, anthraniliate nitroester, anthranilic ketone, or anthranilic nitro ketone; and (c) reacting the product of (b) with an organometallic nucleophile.

In still another embodiment, the present invention provides method for producing 6-(cyanopyrrole)-cyclocarbamate and cyclothiocarbamate compounds according to Scheme 3, where substituents R and CC$^+$ are defined above.

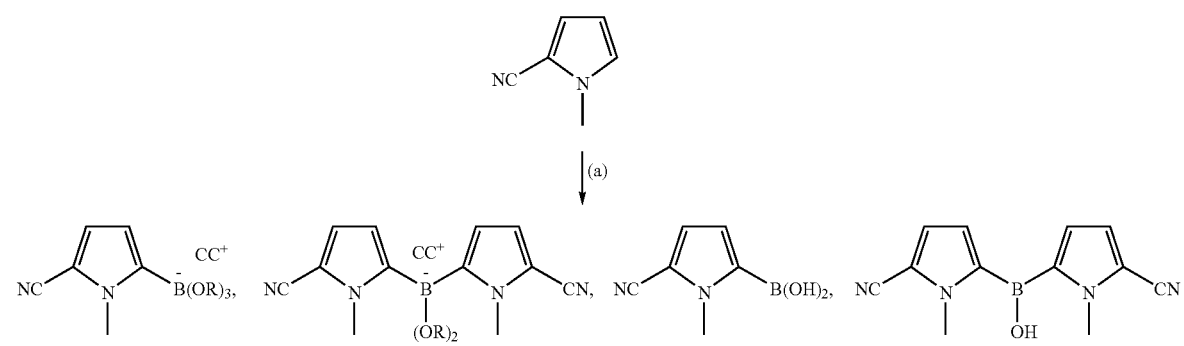

Scheme 3

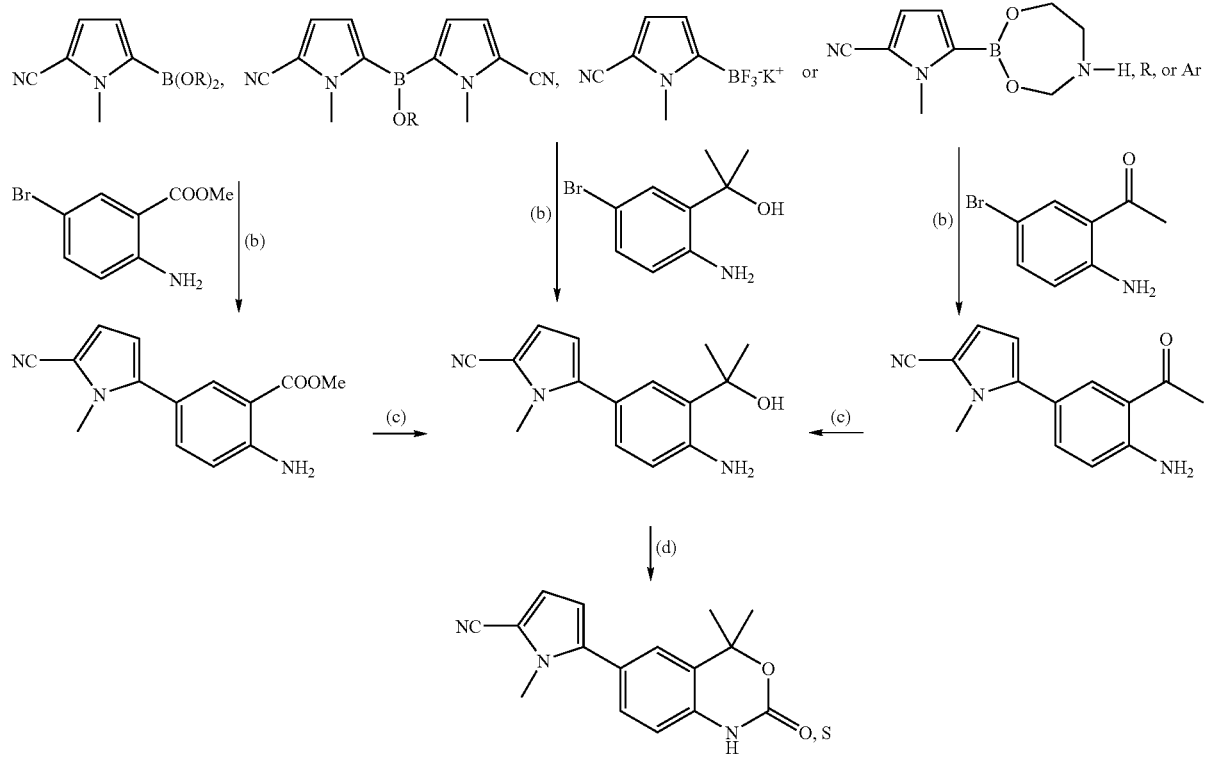

-continued

III. Compounds of the Invention

The present invention also provides novel compounds that can be prepared according to the present invention. In one embodiment, 2-amino-5-(5-cyano-1-methyl-1H-pyrrol-2-yl) benzoic acid methyl ester and 5-[4-amino-3-(1-hydroxy-1-methyl-ethyl)-phenyl]-1-methyl-1H-pyrrole-2-carbonitrile can be prepared according to the methods described above.

Such compounds can be utilized in situ in solution, isolated as raw materials and utilized without further purification, or isolated and purified to obtain pure compounds. Purification can include utilizing techniques known to those of skill in the art, including chromatography, such as thin layer chromatography (TLC) and liquid chromatography (LC) including high performance liquid chromatography (HPLC), extraction, recrystallization, washing, and drying.

IV. Methods of Using the Compounds of the Invention

The compounds of this invention, including intermediates thereof, are modulators of the progesterone receptor (PR), including antagonists and agonists, as described in U.S. Pat. Nos. 6,509,334; 6,566,358; 6,436,929; 6,407,101; and 6,562,857. The compounds of the invention act as PR modulators in functional models, or in-vitro and in-vivo. These compounds are useful for contraception, in the treatment of fibroids, endometriosis, breast, uterine, ovarian and prostate cancer, and in preparing medicaments therefor, and hormone replacement therapy including peri- and post-menopausal hormone replacement therapy.

The compounds of the present invention are used in the form of salts derived from pharmaceutically or physiologically acceptable acids or bases. These salts include, but are not limited to, the following salts with mineral or inorganic acids such as hydrochloric acid, sulfuric acid, nitric acid, phosphoric acid and organic acids such as acetic acid, oxalic acid, succinic acid, and maleic acid. Other salts include salts with alkali metals or alkaline earth metals, such as sodium, potassium, calcium or magnesium in the form of esters, carbamates and other conventional "pro-drug" forms, which, when administered in such form, convert to the active moiety in vivo.

This invention includes pharmaceutical compositions comprising one or more compounds of this invention and a pharmaceutically acceptable carrier or excipient. The invention also includes methods of treatment which comprise administering to a mammal a pharmaceutically effective amount of one or more compounds as described above as modulators of the progesterone receptor, or use of compounds of the invention in the preparation of medicaments useful in treating the above conditions.

The compounds of the present invention, used alone or in combination, are utilized in methods of contraception and the treatment and/or prevention of benign and malignant neoplastic disease. Specific uses of the compounds and pharmaceutical compositions of invention include the treatment and/or prevention, or preparation of medicaments useful therefor, of dysfunctional bleeding, uterine myometrial fibroids, uterine leiomyomata, endometriosis, benign prostatic hypertrophy, polycystic ovary syndrome, carcinomas and adenocarcinomas of the endometrium, ovary, breast, colon, prostate, pituitary, meningioma and other hormone-dependent tumors. Additional uses of the compounds of the present invention include the synchronization of the estrus in livestock and the stimulation of food intake.

When the compounds are employed for the above utilities, they are combined with one or more pharmaceutically acceptable carriers or excipients, for example, solvents, diluents and the like, and are administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations contain, for example, from about 25 to about 90% of the active ingredient in combination with the carrier, more usually between about 5% and 60% by weight.

The effective dosage of active ingredient employed varies depending on the particular compound employed, the mode of administration and the severity of the condition being treated. However, in one embodiment, satisfactory results are obtained when the compounds of the invention are administered at a daily dosage of from about 0.5 to about 500 mg/kg of animal body weight, or administered in divided doses two to four times a day, or in a sustained release form. For most large mammals, the total daily dosage is from about 1 to 100 mg, or about 2 to 80 mg. Dosage forms suitable for internal use comprise from about 0.5 to 500 mg of the active compound in intimate admixture with a solid or liquid pharmaceutically acceptable carrier. This dosage regimen is adjusted to provide the optimal therapeutic response. For example, several divided doses are administered daily or the dose is proportionally reduced as indicated by the exigencies of the therapeutic situation.

These active compounds are administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions are advantageously included, such as flavoring agents, coloring agents, preserving agents, and antioxidants, for example, vitamin E, ascorbic acid, BHT and BHA.

In one embodiment, solid pharmaceutical compositions are used for ease of preparation and administration. In a further embodiment, tablets and hard-filled or liquid-filled capsules are used. In still another embodiment, compounds are administered orally.

In other embodiments, these active compounds are administered parenterally or intraperitoneally. In a further embodiment, solutions or suspensions of these active compounds as a free base or pharmacologically acceptable salt are prepared in water suitably mixed with a surfactant such as hydroxypropylcellulose. In other embodiments, dispersions are prepared, such as in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form is sterile and fluid to the extent that easy syringe ability exits. It is stable under conditions of manufacture and storage and is preserved against the contaminating action of microorganisms such as bacteria and fungi. The carrier is a solvent or dispersion medium containing, for example, water, ethanol (e.g., glycerol, propylene glycol and liquid polyethylene glycol), suitable mixtures thereof, and vegetable oil.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

PREPERATION OF 2-AMINO-5-(5-CYANO-1-METHYL-1H-PYRROL-2-YL) BENZOIC ACID METHYL ESTER

1-Methylpyrrole-2-carbonitrile (0.106 g, 1.0 mmol), triisopropyl borate (270 μL, 1.2 mmol) and tetrahydrofuran (THF-4 mL) were mixed in a 50-mL flask equipped with nitrogen inlet, magnetic stirrer, and temperature controller. After cooling the solution to −3° C., 2M LDA solution (0.6 mL, 1.2 mmol) was added dropwise and the mixture was allowed to warm up to ambient temperature. Toluene (5 mL) was added followed by tetrakis(triphenylphosphine)palladium (25 mg), ethanol (1.6 mL), potassium carbonate (0.326 g), water (2 mL), and methyl bromoanthranilate (0.225 g, 0.98 mmol). The reaction mixture was heated to a gentle reflux for 7 h, then cooled and quenched with 5% hydrochloric acid (HCl), 10% ammonium chloride. It was extracted twice with ethyl acetate. The combined organic phase was washed with brine, dried over magnesium sulfate, filtered, and evaporated to give a dark, very viscous oil (0.307 g), containing 2-amino-5-(5-cyano-1-methyl-1H-pyrrole-2-yl) benzoic acid methyl ester.

Example 2

PREPARATION OF 5-[4-AMINO-3-(1-HYDROXY-1-METHYL-ETHYL)-PHENYL]-1-METHYL-1H-PYRROLE-2-CORBONITRILE

In a similar preparation, starting with 1-methylpyrrole-2-carbonitrile (0.104 g, 0.98 mmol), bromoanthranilic alcohol (0.245 g, 1.1 mmol) was coupled in the presence of tetrakis (triphenylphosphine)palladium (32 mg). After standard work up and evaporation, a glassy mass (0.198 g, about 93% yield), containing cyanopyrroleaniline alcohol, was obtained.

Example 3

PREPARATION OF 6-BROMO-4,4-DIMETHYL-2-THIOXO-1,4-DIHYDRO-BENZOXAZINE 2-(2-Amino-5-bromophenyl)-propan-2-ol (1.028 g, 4.4 mmol) was dissolved in THF (12 mL) and TCDI (1.087 g, 6.1 mmol) was added as solid to form a hazy solution. After stirring the mixture for 140 min., it was transferred into a separatory funnel containing 5% HCl. After separation of the phases, the aqueous phase was extracted twice with 1:1 ethyl acetate/THF. The combined organic extracts were washed with brine and dried over MgSO4. Filtration and evaporation gave 1.081 g (89% yield) of the product.

Example 4

PREPARATION OF (4,4-DIMETHYL-2-THIOXO-1,4-DIHYDRO-2H-3,1-BENZOXAZIN-6-yl)-1H-PYRROLE-2-CARBONITRILE AND (4,4-DIMETHYL-2-OXO-1,4-DIHYDRO-2H-3,1-BENZOXAZIN-6-YL)-1H-PYRROLE-2-CARBONITRILE

5-[4-amino-3-(1-hydroxy-1-methyl-ethyl)-phenyl]-1-methyl-1H-pyrrole-2-carbonitrile prepared according to Example 2 is dissolved in THF and TCDI or CDI is added. Extraction using an aqueous dilute hydrochloride solution gives an about quantitative yield of (4,4-dimethyl-2-thioxo-1,4-dihydro-2H-3,1-benzoxazin-6-yl)-1H-pyrrole-2-carbonitrile and (4,4-dimethyl-2-oxo-1,4-dihydro-2H-3,1-benzoxazin-6-yl)-1H-pyrrole-2-carbonitrile, respectively.

Example 5

SELECTIVE ADDITION OF METHYL GRIGNARD TO METHYL ANTHRANILATE IN THE PRESENCE OF 1-METHYL-1H-PYRROLE-2-CARBONITRILE

1-Methylpyrrole-2-carbonitrile (0.302 g, 2.85 mmol) was dissolved in THF (6 mL). Methyl anthranilate (0.425 g, 2.81 mmol) was added, followed by the addition of 1.4M solution of methylmagnesium bromide in toluene/THF 75/25 (4 mL, 5.6 mmol, 2 eq.) at about −7° C. After standard work up and evaporation, the product (0.695 g) was isolated as a 1:1 mixture of 1-methyl-1H-pyrrole-2-carbonitrile and 2-(2-aminophenyl)propan-2-ol.

All publications identified in this specification are incorporated herein by reference. While the invention has been described with reference to specific embodiments, it will be appreciated that modifications can be made without departing from the spirit of the invention. Such modifications are intended to fall within the scope of the appended claims.

What is claimed is:

1. A method for producing 6-(cyanopyrrole)-cyclocarbamate or cyclothiocarbamate compounds comprising the steps of:
   (a) reacting a cyanopyrrole with a coupling agent;
   (b) reacting the product of step (a) with an anthranilic alcohol or anthranilic nitro alcohol to form a cyanopyrrole substituted anthranilic alcohol or a cyanopyrrole substituted anthranilic nitro alcohol; and
   (c) optionally reducing the cyanopyrrole substituted anthranilic nitro alcohol to the cyanopyrrole substituted anthranilic alcohol; and
   (d) converting the cyanopyrrole substituted anthranilic alcohol to said 6-(cyanopyrrole)-cyclocarbamate or cyclothiocarbamate compound.

2. The method according to claim 1, wherein said anthranilic alcohol is bromoanthranilic alcohol.

3. The method according to claim 1, wherein said anthranilic alcohol is 4-bromo-methylanthranilic alcohol.

4. The method according to claim 1, wherein said anthranilic alcohol or nitro alcohol thereof is:

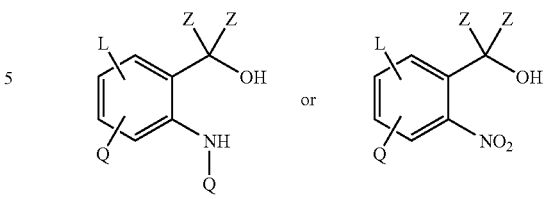

wherein:
Z are, independently, H, $C_1$ to $C_6$ alkyl, substituted $C_1$ to $C_6$ alkyl, or $COR^A$;
$R^A$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
Q, independently, H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ alkoxy, substituted $C_1$ to $C_6$ alkoxy, $C_1$ to $C_6$ aminoalkyl, substituted $C_1$ to $C_6$ aminoalkyl, or $COR^B$;
$R^B$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
L is halogen or $OSO_2R^1$; and
$R^1$ is H, $C_1$ to $C_6$ alkyl, or substituted $C_1$ to $C_6$ alkyl.

5. The method according to claim 1, wherein the cyanopyrrole substituted anthranilic alcohol is formed by:
   (i) reacting the product of (a) with an anthranilate or nitroester thereof to form a cyanopyrrole substituted anthranilate or nitroester thereof; and
   (ii) reacting the cyanopyrrole substituted anthranilate or nitroester thereof with an organometallic nucleophile.

6. The method according to claim 5, wherein the anthranilate is a bromoanthranilate.

7. The method according to claim 5, wherein said anthranilate is 4-bromo-methylanthranilate.

8. The method according to claim 5, wherein said anthranilate or nitroester thereof is:

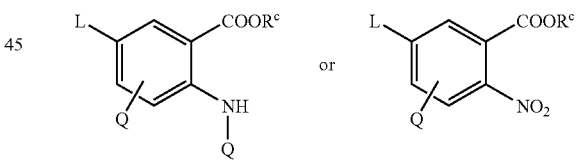

wherein:
Q are, independently, H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ alkoxy, substituted $C_1$ to $C_6$ alkoxy, $C_1$ to $C_6$ aminoalkyl, substituted $C_1$ to $C_6$ aminoalkyl, or $COR^B$;
$R^B$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
$R^C$ is $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ aminoalkyl, or substituted $C_1$ to $C_6$ aminoalkyl;
L is halogen or $OSO_2R^1$; and
$R^1$ is H, $C_1$ to $C_6$ alkyl, or substituted $C_1$ to $C_6$ alkyl.

9. The method according to claim 1, wherein step (d) is performed using phosgene, thiophosgene, triphosgene, 1,1'-carbonyldiimidazole (CDI), 1,1'-thiocarbonyldiimidazole (TCDI), carbon disulfide, or carbon disulfide in the presence of a base.

10. The method according to claim 1, wherein said cyanopyrrole is:

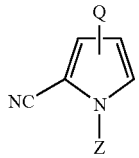

wherein:
Z is H, $C_1$ to $C_6$ alkyl, substituted $C_1$ to $C_6$ alkyl, or $COR^A$;
$R^A$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
Q is H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ alkoxy, substituted $C_1$ to $C_6$ alkoxy, $C_1$ to $C_6$ aminoalkyl, substituted $C_1$ to $C_6$ aminoalkyl, or $COR^B$; and
$R^B$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl.

11. The method according to claim 1, wherein said cyanopyrrole is 1-methyl-2-cyanopyrrole.

12. The method according to claim 1, wherein said coupling agent is a trialkyl borate.

13. The method according to claim 1, wherein the product of step (a) is:

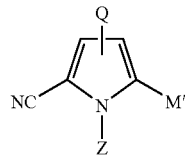

wherein:
M' is a boron, zinc, magnesium or silicon containing coupling group;
Z is H, $C_1$ to $C_6$ alkyl, substituted $C_1$ to $C_6$ alkyl, or $COR^A$;
$R^A$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
Q is H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ alkoxy, substituted $C_1$ to $C_6$ alkoxy, $C_1$ to $C_6$ aminoalkyl, substituted $C_1$ to $C_6$ aminoalkyl, or $COR^B$; and
$R^B$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl.

14. The method according to claim 1, wherein the product of step (a) is (5-cyano-1-methyl-1H-pyrrol-2-yl) boronic acid.

15. The method according to claim 1, wherein said 6-(cyanopyrrole)-cyclocarbamate compound is:

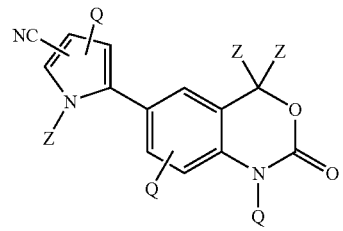

wherein:
Z are, independently, H, $C_1$ to $C_6$ alkyl, substituted $C_1$ to $C_6$ alkyl, or $COR^A$;
$R^A$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
Q are, independently, H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ alkoxy, substituted $C_1$ to $C_6$ alkoxy, $C_1$ to $C_6$ aminoalkyl, substituted $C_1$ to $C_6$ aminoalkyl, or $COR^B$; and
$R^B$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl.

16. The method according to claim 1, wherein said 6-(cyanopyrrole)-cyclothiocarbamate compound is:

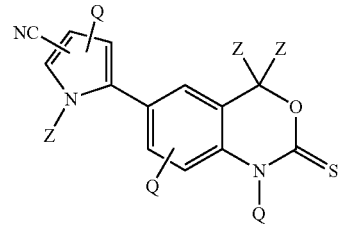

wherein:
Z are, independently, H, $C_1$ to $C_6$ alkyl, substituted $C_1$ to $C_6$ alkyl, or $COR^A$;
$R^A$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
Q are, independently, H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ alkoxy, substituted $C_1$ to $C_6$ alkoxy, $C_1$ to $C_6$ aminoalkyl, substituted $C_1$ to $C_6$ aminoalkyl, or $COR^B$; and
$R^B$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl.

17. The method according to claim 1, wherein said 6-(cyanopyrrole)-cyclothiocarbamate compound is 5-(4,4-dimethyl-2-thioxo-1,4-dihydro-2H-benzooxazin-6-yl)-1-methyl-1H-pyrrole-2-carbonitrile, or a pharmaceutically acceptable salt thereof and said 6-(cyanopyrrole)-cyclocarbamate compound is 5-(4,4-dimethyl-2-oxo-1,4-dihydro-2H-benzooxazin-6-yl)-1-methyl-1H-pyrrole-2-carbonitrile, or a pharmaceutically acceptable salt thereof.

* * * * *

UNITED STATES PATENT AND TRADEMARK OFFICE
CERTIFICATE OF CORRECTION

PATENT NO. : 7,582,755 B2
APPLICATION NO. : 11/113795
DATED : September 1, 2009
INVENTOR(S) : B. Wilk It is certified that error appears in the above-identified patent and that said Letters Patent is hereby corrected as shown below:

(1) Col. 26, Claim 4, lines 5-10, replace the following chemical structures:

" 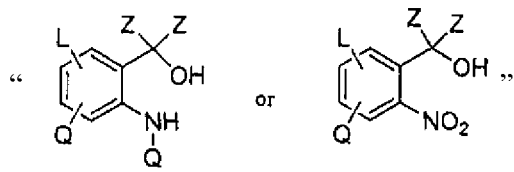 or 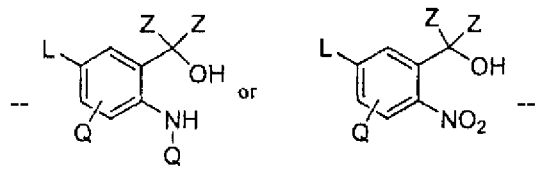 ,, with the following:

-- 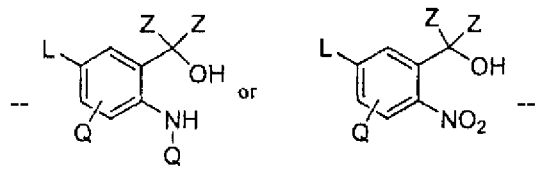 or 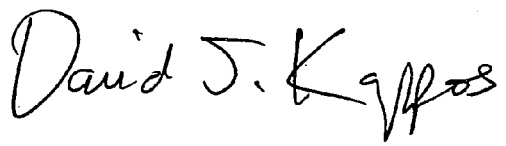 --

Signed and Sealed this

Thirteenth Day of October, 2009

David J. Kappos
*Director of the United States Patent and Trademark Office*

UNITED STATES PATENT AND TRADEMARK OFFICE
CERTIFICATE OF CORRECTION

PATENT NO.       : 7,582,755 B2                                        Page 1 of 1
APPLICATION NO.  : 11/113795
DATED            : September 1, 2009
INVENTOR(S)      : Bogdan Kazimierz Wilk It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1142 days.

Signed and Sealed this

Fourteenth Day of September, 2010

David J. Kappos
*Director of the United States Patent and Trademark Office*